US006280702B1

(12) United States Patent
Carter et al.

(10) Patent No.: US 6,280,702 B1
(45) Date of Patent: Aug. 28, 2001

(54) ENDOSCOPY TISSUE STAIN

(75) Inventors: Frank C. Carter, Wormleysburg; Frank W. Jackson, Mechanicsburg, both of PA (US); Robert G. Whalen, Willington, CT (US)

(73) Assignee: Chek-Med Systems, Inc., Camp Hill, PA (US)

( * ) Notice: Subject to any disclaimer, the term of this patent is extended or adjusted under 35 U.S.C. 154(b) by 0 days.

(21) Appl. No.: 09/303,164

(22) Filed: Apr. 30, 1999

(51) Int. Cl.$^7$ ..................................................... A61K 49/00
(52) U.S. Cl. ......................... 424/9.1; 424/1.11; 600/101; 606/45
(58) Field of Search ................................. 424/1.11, 9.1, 424/9.2; 600/101, 103, 104, 184, 920; 502/180; 606/45; 423/445 R, 449.1

(56) References Cited

U.S. PATENT DOCUMENTS 5,122,147    6/1992    Sewell, Jr. .
5,542,948    8/1996    Weaver et al. .

OTHER PUBLICATIONS

Lewis, Sr, Hawley's Condensed Chemical Dictionary, Twelfth Edition, pp. 217–218, 1993.*
Naveau, S.; Bonhomme, L.; Preaux, N.; Chaput, J–C., "A pure charcoal suspension for colonoscopic tatto," Gastrointestinal Endoscopy, vol. 37 (No. 6), pp. 624–625, 1991.
Shatz, BA; Weinstock, LB; Swanson, PE; Thyssen, EP, "Long–term safety of India ink tattoos in the colon," Gastrointestinal Endoscopy, vol. 45 (No. 2), pp. 153–156, 1997.
Nizam, R; Siddiqi, N.; Landas, SK; Kaplan, DS; Holtzapple, PG, "Colonic Tattooing with Inda Ink: Benefits, Risks, and Alternatives," The American Journal of Gastroenterology, vol. 91 (No. 9), pp. 1804–1808, 1996.
Salomon, P; Berner, JS; Waye, JD, "Endoscopic India ink injection: a method for preparation, sterilization, and administration," Gastrointestinal Endoscopy, vol. 39 (No. 6), pp. 803–805, 1993.
Park, SI; Genta, RS; Romeo, DP; Weesner, RE, "Colonic abscess and focal peritonitis secondary to India ink tatooing of the colon," Gastrointestinal Endoscopy, vol. 37 (No. 1), pp. 68–70, 1991.
Botoman, VA; Pietro, M; Thirlby, RC, "Localization of Colonic Lesions with Endoscopic Tattoo," Dis. Colon Rectum, pp. 775–776, Aug. 1994.
Hammond, DC; Lane, FR; Mackeigan, JM; Passinault, WJ, "Endoscopic Tattoing of the Colon: Clinical Experience," The American Surgeon, pp. 205–210, Mar. 1993.
Hyman, N; Waye, JD, "Endoscopic four quadrant tattoo for the identification of colonic lesions at surgery," Gastrointestinal Endoscopy, vol. 37 (No. 1) pp. 56–58, 1991.
Ponsky, JL; King, JF, "Endoscopic marking of colonic lesions," Gastrointestinal Endoscopy, vol. 22 (No. 1), pp. 42–43, 1975.
Technology Assessment Status Evaluation, "Endocsopic Tissue Staining and Tattooing", American Society for Gastrointestinal Endoscopy, 6 pages, Oct. 1995.
Goldman, EL, "India Ink Marks the Spot in Polypectomy," Internal Medicine News, p. 50, Feb. 1, 1997.
Lightdale, CJ, "India ink colonic tatto: blots on the record," Gastrointestinal Endoscopy, vol. 37 (No. 1), pp. 99–100, 1991.

* cited by examiner

*Primary Examiner*—Dameron L. Jones
(74) *Attorney, Agent, or Firm*—Eugene Chovanes

(57) ABSTRACT

An endoscopic tissue staining composition comprises carbon and suspending/viscosity-increasing agent in a pharmaceutically acceptable delivery vehicle. In an embodiment, the composition includes carbon black, activated carbon or unactivated carbon, suspending/viscosity-increasing agent, anti-foaming agent and surfactant. In a particular embodiment, the composition includes 0.01% to 1.0% carbon, 5.0% to 25% suspending/viscosity-increasing agent such as glycerol, 0.005% to 0.05% anti-foaming agent such as simethicone, 0.5% to 1.5% surfactant such as polyoxyethylene sorbitan esterified with fatty acid, and water.

A method for staining of internal sites, particularly in the mucosal layers of the gastrointestinal tract, urinary bladder or lungs, includes injecting the composition in staining amount in proximity to the internal site. A kit includes the composition packaged with a means for endoscopic injection, preferably a syringe and sclerotherapy needle.

17 Claims, No Drawings

ENDOSCOPY TISSUE STAIN

The invention relates to a permanent stain for marking of internal sites for endoscopic identification, e.g., in the gastrointestinal tract, bladder, or lungs. The invention also includes a method and kit for marking of the sites.

At present, there is an absence of FDA approved marking compositions formulated especially for use in endoscopy for the staining of internal sites in the body. Endoscopists have had to make do by adapting their techniques to use commercially available writing inks and other standard stains which are not approved for use in humans. Available approved stains are not permanent markers.

Endoscopic stains including Lugol's solution, methylene blue, toluidine blue, congo red, phenol red, indigo carmine and India ink are described by the American Society for Gastrointestinal Endoscopy (ASGE) in *Technology Assessment Status Evaluation, Endoscopic Tissue Staining and Tattooing,* published by American Society for Gastrointestinal Endoscopy, Manchester, Mass., October 1995. The only known permanent stain for endoscopic tattooing is India ink. The use of India ink to endoscopically label colonic lesions was first described by J. L. Ponsky and J. F. King, *Gastrointest Endosc.* 1975, 22:42–3. India ink has also been used for marking esophageal lesions as described by R. T. Shaffer et al., *Gastrointest. Endosc.* 1998, 47:257–260.

It was found that other permanent fountain pen inks are not an acceptable substitute for commercially available India ink. E. L. Goldman, *Internet Medicine News,* Feb. 1, 1997, p. 50.

The compositions of various commercially available India inks and comparisons of their use in endoscopic tattooing of the colon have been described by P. S. Salomon et al., *Gastrointest. Endosc.* 1991, 39(6): 803–804. The composition of India ink made by Higgins (Faber-Castell, Lewisberg, Tenn.) is described as containing about 7% carbon pigment, 5% propylene glycol and smaller concentrations of shellac, ammonium hydroxide and surfactant and when the composition was diluted in equal parts (50:50) with bacteriostatic water, it caused an inflammatory response. The composition of India ink made by Pelikan (Hanover, Germany) is described as containing ethylene glycol, sodium tetraborate decahydrate, ammonia and gelatin, and when diluted in 1:10 dilution in sterile water, it caused an abscess. India ink made by Koh-I-Noor (Bloomsburg, N.J.) is described as composed of carbon particles (approximately 7% by weight) with stabilizing diluents present in all commercial products, including ethylene glycol methyltert-butyl ether (Methyl Carbitol), phenol, ammonium hydroxide and shellac, and was diluted 1:100 with 0.9% normal saline solution and successfully tested by Salomon et al. An attempt by Salomon et al. to test a "homemade" India ink of dry carbon pigment, 0.1% by weight mixed with normal saline solution was unsuccessful.

Although some endoscopists have found small volumes of India ink for tattooing of the colon to be safe (see, e.g., B. A. Shatz, *Gastrointest. Endosc.* 1997, 45(2): 153–156), others have found complications following colonoscopic India ink injection. V. A. Botoman et al. 1994, *Dis. Colon Rectum* 37:775–776; J. Lightdale, *Gastrointest. Endosc.* 1991, 37(1): 99–100; S. I. Park et al., *Gastrointest. Endosc.* 1991, 37(1): 68–70.

Following reports of complications using India ink, some have looked for alternatives. A pure suspension of charcoal was tested for colonoscopic tattoo, using 5% weight/volume aqueous suspension of micronized charcoal particles. S. Naveau et al. 1991, *Gastrointest. Endosc.* 1991, 37(6): 624–25. Indocyanine green was also used for the marking of lesions of the colon by D. C. Hammond, et al., *The American Surgeon* 1993, 59(3): 205–210, but this stain does not have long term permanence. Problems still remain in endoscopic tissue marking.

It is an object of the invention to provide an improved endoscopic tissue staining composition for permanent marking of internal sites in the body.

It is a further object of the invention to provide a staining composition which can be used at internal sites with no adverse effects.

SUMMARY OF THE INVENTION

An endoscopic tissue staining composition comprises carbon particles in a pharmaceutically acceptable delivery vehicle. The carbon is in an effective amount for substantially permanent staining of internal mucosa or other sites in the body, preferably in an amount from about 0.01% to 1.0% based on weight. In a preferred embodiment, the carbon particles are carbon black. Also in a preferred embodiment, the composition includes a suspending/viscosity-increasing agent in an amount sufficient for suspending the carbon particles in solution. Preferred suspending/viscosity-increasing agents include glycerol, propylene glycol, isopropylene glycol, polyethylene glycol or cellulose.

An embodiment of the invention includes a composition comprising carbon particles, suspending/viscosity-increasing agent, anti-foaming agent and surfactant, respectively in internal staining, suspending/viscosity-increasing, anti-foaming and surface-active amounts, prepared in a pharmaceutically acceptable vehicle, preferably water. The carbon preferably includes amorphous carbon powders such as carbon black and activated or unactivated (nonactivated) carbon. Carbon is "activated" by heating to about 800–900° C. resulting in a porous internal structure. "Unactivated" carbon is not treated this way. Preservative may also be added in anti-microbial amounts.

In a particularized embodiment, the composition comprises:

0.01% to 1.0% carbon, preferably 0.1% to 1.0%,

5% to 25% suspending/viscosity-increasing agent, preferably 10% to 20%, 0.005% to 0.05% anti-foaming agent, preferably 0.01% to 0.04%, 0.5% to 1.5% surfactant, preferably 0.75% to 1.25%, zero to 2.0% preservative, preferably 0.5% to 1.5%, and sufficient water, for example, about 70% to 90%, for a 100% composition. All percentages herein are based on weight. The carbon is carbon black, activated or unactivated carbon.

In a preferred embodiment, the suspending/viscosity-increasing agent is glycerol, the anti-foaming agent is simethicone, the surfactant is esterified polyoxyethylene sorbitan, and the anti-microbial is benzyl alcohol. Therefore this embodiment of the invention comprises 0.01% to 1.0% carbon, preferably 0.01% to 1.0%, 5% to 25% glycerol, preferably 10% to 20%, 0.005% to 0.05% simethicone, preferably 0.01% to 0.04%, 0.5% to 1.5% polyoxyethylene sorbitan esterified with fatty acid, preferably 0.75% to 1.25%, zero to 2.0% benzyl alcohol, preferably 0.5% to 1.5%, and sufficient water for a 100% composition.

The composition is used for marking internal sites, e.g., in the gastrointestinal tract, urinary bladder or bronchi.

A method for marking or tattooing of internal sites, e.g., in the gastrointestinal tract, urinary bladder or lungs for endoscopic identification includes injecting a staining amount of the composition of the invention comprising carbon black in a pharmaceutically acceptable delivery vehicle such as water. In another embodiment, the injected composition includes carbon, humectant, anti-foaming agent and surfactant, respectively in staining, wetting, anti-foaming, and surface-active amounts, injected in proximity to the site. Preferred embodiments for the method utilize the compositions of the inventions described above. In a particularized embodiment, the method for marking internal sites comprises injecting the site with a composition comprising 0.01% to 1.0% carbon, preferably 0.01% to 1.0%, 5% to 25% suspending/viscosity-increasing agent, preferably 10% to 20%, 0.005% to 0.05% anti-foaming agent, preferably 0.01% to 0.04%, 0.5% to 1.5% surfactant, preferably 0.75% to 1.25%, zero to 2.0% preservative, preferably 0.5% to 1.5%, and sufficient water, for example, about 70% to 90%, for a 100% composition. The carbon is carbon black, activated or unactivated carbon.

In a preferred embodiment for a method of marking internal sites, the suspending/viscosity-increasing agent is glycerol, the anti-foaming agent is simethicone, the surfactant is esterified polyoxyethylene sorbitan, and the anti-microbial is benzyl alcohol. Therefore this embodiment of the method of the invention includes injecting a composition comprising 0.01% to 1.0% carbon, preferably 0.1% to 1.0%, 5% to 25% glycerol, preferably 10% to 20%, 0.005% to 0.05% simethicone, preferably 0.01% to 0.04%, 0.5% to 1.5% polyoxyethylene sorbitan esterified with fatty acid, preferably 0.75% to 1.25%, zero to 2.0% benzyl alcohol, preferably 0.5% to 1.5%, and sufficient water for a 100% composition.

Injection may be made, for example, tangentially to a site, proximally and distally to a site, or in all four quadrants of the lumen around the site. The total amount to be injected can be determined by the skilled artisan and can be, for example, from about 0.5 ml to about 5.0 ml.

A kit for endoscopic tissue staining or tattooing of internal sites, e.g., in the gastrointestinal tract, urinary bladder or lungs, includes the composition of the invention which comprises carbon particles in a pharmaceutically acceptable delivery vehicle such as water, packaged with a means for endoscopic injection. Another embodiment of the kit includes a composition comprising carbon particles, suspending/viscosity-increasing agent, anti-foaming agent and surfactant, respectively in staining, suspending/viscosity-increasing, anti-foaming, and surface-active amounts, containerized and packaged with a means for endoscopic injection. In a particularized embodiment, the kit includes a composition comprising 0.01% to 1.0% carbon, preferably 0.1% to 1.0%, 5% to 25% suspending/viscosity-increasing agent, preferably 10% to 20%, 0.005% to 0.05% anti-foaming agent, preferably 0.01% to 0.04%, 0.5% to 1.5% surfactant, preferably 0.75% to 1.25%, zero to 2.0% preservative, preferably 0.5% to 1.5%, and sufficient water for a 100% composition.

The carbon is carbon black, activated or unactivated carbon. A preferred means for injection includes a syringe and sclerotherapy needle. A catheter is also useful for reaching internal sites.

More preferably, the kit includes the composition of the invention as described above wherein the suspending/viscosity-increasing agent is glycerol, the anti-foaming agent is simethicone, the surfactant is esterified polyoxyethylene sorbitan, and the anti-microbial is benzyl alcohol, and the composition comprises 0.01% to 1.0% carbon, preferably 0.1% to 1.0%, 5% to 25% glycerol, preferably 10% to 20%, 0.005% to 0.05% simethicone, preferably 0.01% to 0.04%, 0.5% to 1.5% polyoxyethylene sorbitan esterified with fatty acid, preferably 0.75% to 1.25%, zero to 2.0% benzyl alcohol, preferably 0.5% to 1.5%, and sufficient water for a 100% composition.

The composition is containerized and packaged with a syringe, sclerotherapy needle and catheter, to be used in conjunction with an endoscope, sigmoidoscope or colonoscope.

Advantageously, the composition of the invention is free of toxins and antigens, and is inert and safe for use in humans, has high contrast and low viscosity, and resists diffusion when injected.

DETAILED DESCRIPTION OF THE INVENTION

An endoscope traditionally includes a bundle of light transmitting fibers in conjunction with a telescopic lens system so that the device has an image receiving end and an insertion end. Currently, more advanced video systems are used in which an optically sensitive chip collects the image and presents an image on a video screen via computer digital technology. An endoscopist or surgeon can examine internal body tissues by guiding the insertion tube end to the desired location in the body and observing through the viewing end, or more commonly on a viewing screen via computer digital technology. Endoscopes are available for various specialized purposes. For example, there are upper endoscopes for examining the esophagus, stomach and duodenum, urethroscopes for examining the urethra and bladder, colonoscopes for examining the colon, angioscopes for examining the blood vessels and heart, bronchoscopes for examining the bronchi, laparoscopes for examining the joint spaces, and sigmoidoscopes for examining the rectum and sigmoid colon. Endoscopes can also include channels for delivery of air, liquid and suction, biopsy instruments, graspers and other instruments. Endoscopes are known in the art and described, for example, in U.S. Pat. Nos. 5,681,262, 5,025,778, 4,748,970, 4,468,216 and 4,146,019.

When a cancer is found in the gastrointestinal tract, urinary bladder or bronchi of the lungs, marking of the site is used to guide the surgeon to the site. Moreover, polyps in the colon are generally promptly removed because of their potential for malignancy. Polyps are discrete mass lesions that protrude into the intestinal lumen. Mucosal neoplastic (adenomatous) polyps give rise to adenocarcinoma of the colon and therefore, polyps detected at sigmoidoscopy or barium enema are removed as soon as possibly by colonoscopic polypectomy or other techniques such as those described in U.S. Pat. Nos. 5,122,147 and 5,542,948. Sometimes polyps or tumors cannot be safely or completely removed by colonoscopy, and surgical resection must follow. Once the polyps have been removed, surveillance colonoscopy is periodically repeated to look for missed polyps, new adenomas, residual or recurrent cancer.

Cancerous lesion sites or potentially cancerous lesion sites are marked because on follow-up it can be difficult to localize the lesion sites. Therefore, a marking composition must be relatively permanent to enable the surgeon to find the exact site at a later time.

It has been discovered that the disadvantages of India ink can be overcome by using a composition comprising carbon particles as pigment in a pharmaceutically acceptable carrier. Another embodiment of the invention includes carbon, suspending/viscosity-increasing agent, anti-foaming agent and surfactant, and the carbon is carbon black, activated or unactivated carbon. Carbon black, activated and unactivated carbon are amorphous forms of carbon and are described, for example, in the Kirk-Othmer *Concise Encyclopedia of Chemical Technology*, D. Eckroth et al. ed., John Wiley & Sons, New York 1985, at pages 204–209. Amorphous forms of carbon, i.e., carbon forms which are poorly developed in crystallinity, include carbon black, coke and charcoal. These all can be used in the form of particles or powder but differ in the manner in which they are made.

Carbon black is finely divided carbon such as vaporized heavy oil fractions produced by burning hydrocarbons using partial oxidation. The pigment can contain over 97% carbon. The oil furnace process represents the most widely used method for producing carbon black. Generally, a liquid hydrocarbonaceous feedstock is sprayed into turbulent products of combustion produced by reacting fluid fuel and oxygen and the hydrocarbon feedstock is converted into carbon black which is separated from combustion gases. Carbon black can also be produced by burning natural gas and letting the flame impinge on a cool surface. The preferred carbon black useful herein is low in incompletely burned hydrocarbons which may be absorbed during manufacture; particularly, the carbon black is low in aromatics and other compounds which may be carcinogens. More particularly, the preferred carbon black is low in residual polycyclic aromatic hydrocarbons. By "low" is meant substantially non-carcinogenic levels.

Charcoal is prepared by the ignition of wood, sugar, and other carbon-containing compounds in the absence of air. It has a graphitic structure but is not well developed in crystallinity. It will therefore be categorized as amorphous herein. Activated carbon is similarly obtained by the carbonization or destructive distillation of vegetable matter, e.g., wood, nut shells, bones, or other carbonaceous material. The carbon is activated by heating to high temperatures in the presence of water or carbon dioxide which results in a carbon having a porous internal structure. Carbon which has not been subjected to this treatment will be called unactivated herein. Coke is prepared by heating coal in the absence of air.

In addition to carbon pigment, the composition includes suspending or viscosity-increasing agent, anti-foaming agent and surfactant. Suspending or viscosity-increasing agents increase viscosity and keep the carbon in solution. Suspending/viscosity-increasing agents include Acacia, Agar, Alginic Acid, Aluminum Monosterate, Attapulgite-Activated, Attapulgite-Colloidal Activated, Bentonite, Bentonite-Purified, Bentonite-Magma, Carbomer 910, Carbomer 934, Carbomer 934P, Carbomer 940, Carbomer 941, Carbomer 1342, Carboxymethylcellulose Calcium, Carboxymethylcellulose Sodium, Carboxymethylcellulose Sodium 12, Carrageenan, Cellulose: Microcrystalline and Carboxymethylcellulose Sodium, Dextrin, Gelatin, Guar Gum, Hydroxyethyl Cellulose, Hydroxypropyl Cellulose, Hydroxypropyl Methylcellulose, Magnesium Aluminum Silicate, Methylcellulose, Pectin, Polyethylene Oxide, Polyvinyl Alcohol, Povidone, Propylene Glycol Alginate, Silicon Dioxide, Silicon Dioxide-Colloidal, Sodium Alginate, Tragacanth, and Xanthan Gum. Other agents to increase viscosity and keep the carbon particles in solution include as non-limiting examples emulsifying or solubilizing agents including Acacia, Cholesterol, Diethanolamine (Adjunct), Glyceryl Monostearate, Lanolin Alcohols, Lecithin, Mono- and Di-glycerides, Monoethanolamine (Adjunct), Oleic Acid (Adjunct), Oleyl Alcohol (Stabilizer), Poloxamer, Polyoxyethlene 50 Stearate, Polyoxyl 35 Castor Oil, Polyoxyl 40 Hydrogenated Castor Oil, Polyoxyl 10 Oleyl Ether, Polyoxyl 20 Cetostearyl Ether, Polyoxyl 40 Stearate, Polysorbate 20, Polysorbate 40, Polysorbate 60, Polysorbate 80, Propylene Glycol Diacetate, Propylene Glycol Monostearate, Sodium Lauryl Sulfate, Sodium Stearate, Sorbitan Monolaurate, Sorbitan Monooleate, Sorbitan Monopalmitate, Sorbitan Monostearate, Stearic Acid, Trolamine, and Wax-Emulsifying. Preferred agents include as non-limiting examples, glycerine (glycerol), propylene glycol, isopropylene glycol, polyethylene glycol and cellulose. Other compatible agents listed in the United States Pharmacopia can also be used. In one embodiment, a preferred suspending or viscosity-increasing agent is glycerol (propane-1,2,3-triol or glycerin) which is a trihydric alcohol soluble in water and alcohol. Preferred is USP (pharmaceutical grade).

The composition includes anti-foaming agent and surfactant which are substantially non-irritating and biocompatible. By biocompatible is meant non-damaging to human tissue.

Preferred anti-foaming agents are dimethicone and simethicone. Simethicone (USP) is described in the USP Dictionary of USAN and International Drug Names, U.S. Pharmacopeia, Rockville, Md., 1997 at page 652 as a mixture of poly(dimethylsiloxane) and silicon dioxide. The poly(dimethylsiloxane) and silicon dioxide. The poly (dimethylsiloxane) is α-(trimethylsilyl)-ω-methyl-poly[oxy (dimethylsilylene)]. The calculated average of dimethylsiloxane units in poly(dimethylsilylene) is 200 to 350. The simethicone is preferably supplied from the USP or FDA acceptable solution.

A preferred surfactant is a non-ionic surfactant which is a polyoxyethylene sorbitan ester obtained by esterification of sorbitol with fatty acid, e.g., monolaurate, monooleate, monopalmitate, monostearate, trioleate and tristearate. Compounds of this type are commercially available as Tweens (20, 21, 40, 60, 65, 80, 80R, 85) (ICI American, Wilmington, Del.). Tween 80 is preferred.

The composition may also include a suitable preservative such as benzyl alcohol, methyl or ethyl paraben, or benzalkonium chloride, which can function as an antimicrobial.

Other pharmaceutically acceptable excipients may be added, e.g., buffers such as citrate or phosphate buffering agents.

The composition is prepared by mixing the components in a pharmaceutically acceptable vehicle suitable for internal injection such as water, and preferably sterilizing by known methods, e.g., autoclaving, or radiation, or the components may be sterilized separately before mixing. The composition has a sufficiently low viscosity to allow injection through a long transendoscopic catheter such as a sclerotherapy needle.

The composition is used in the form of a liquid surgical marker for endoscopic marking (tattooing) using known endoscopic techniques. For example, the liquid surgical marker can be drawn into a syringe and injected through a sclerotherapy needle long enough to traverse a colonoscope. As non-limiting examples, marking may be done by injecting under the mucosa by oblique penetration once, proximally and distally, or at four quadrants in proximity to the lesion using the tangential 4-quadrant technique.

EXAMPLE

An endoscopic staining composition is prepared by combining 0.2% carbon black,

15% glycerol, 0.02% simethicone, 1.0% polyoxyethylene sorbitan esterified with monooleate (Tween 80), and 1.0% benzyl alcohol; and sterile water for injection.

The composition is endoscopically injected to mark the site of a cancerous or pre-cancerous lesion on the internal mucosa. As a non-limiting example, staining at the internal site can be accomplished with 0.1 to 1 ml per injection site. Placement of the stain is confirmed visually at the injection site as the black stain spreads in the submucosa layer. A kit includes the composition packaged with a syringe and sclerotherapy needle or catheter.

What is claimed is:

1. An endoscopic tissue staining composition comprising carbon pigment, suspending/viscosity-increasing agent in a pharmaceutically acceptable delivery vehicle, anti-foaming agent, and surfactant, said carbon pigment in an effective staining amount for internal mucosa and said suspending/viscosity-increasing agent in an effective amount for suspending carbon in solution and providing sufficient viscosity for endoscopic tissue staining.

2. The composition of claim 1 wherein the suspending/viscosity-increasing agent is selected from the group consisting of glycerol, propylene glycol, isopropylene glycol, polyethylene glycol or cellulose.

3. The composition of claim 1 wherein the anti-foaming agent is selected from the group consisting of dimethicone or simethicone and the surfactant is polyoxyethylene sorbitan esterified with fatty acid.

4. The composition of claim 1 wherein the carbon pigment comprises particles selected from the group consisting of carbon black, activated carbon or unactivated carbon.

5. The endoscopic tissue staining composition of claim 1 comprising 0.01% to about 1.0% carbon pigment, about 5.0% to about 25% suspending/viscosity-increasing agent, about 0.005% to about 0.05% anti-foaming agent, about 0.5% to about 1.5% surfactant, and water to yield 100% composition based on weight.

6. The composition of claim 5 wherein the suspending/viscosity-increasing agent is selected from the group consisting of glycerol, propylene glycol, isopropylene glycol, polyethylene glycol or cellulose, the anti-foaming agent is dimethicone or simethicone, and the surfactant is polyoxyethylene sorbitan esterified with fatty acid.

7. The composition of claim 1 comprising about 0.1% to about 1.0% carbon pigment, about 10% to about 20% suspending/viscosity-increasing agent, about 0.01% to about 0.04% anti-foaming agent, about 0.5% to about 1.5% surfactant, and water to yield 100% composition based on weight.

8. The composition of claim 7 wherein the suspending/viscosity-increasing agent is selected from the group consisting of glycerol, propylene glycol, isopropylene glycol, polyethylene glycol or cellulose, the anti-foaming agent is dimethicone or simethicone, and the surfactant is polyoxyethylene sorbitan esterified with fatty acid.

9. An endoscopic staining composition comprising about 0.01% to about 1.0% carbon black, activated carbon or unactivated carbon, about 5% to about 25% glycerol, about 0.005% to about 0.05% simethicone, about 0.5% to about 1.5% polyoxyethylene sorbitan esterified with fatty acid, zero to about 2.0% benzyl alcohol, and sufficient water for a 100% composition.

10. A method for staining of an internal site comprising injecting the composition of claim 1 in a staining amount in proximity to the site.

11. The method of claim 10 wherein the internal site is selected from the group consisting of gastrointestinal tract, urinary bladder or lungs.

12. A method for staining of an internal site comprising injecting the composition of claim 8 in a staining amount in proximity to the site.

13. The method of claim 12 wherein the internal site is selected from the group consisting of gastrointestinal tract, urinary bladder or lungs.

14. A kit comprising the composition of claim 1 packaged with a means for endoscopic injection.

15. A kit comprising the composition of claim 4 packaged with a means for endoscopic injection.

16. The kit of claim 14 wherein the means for endoscopic injection comprises a syringe and sclerotherapy needle.

17. The composition of claim 1 wherein said carbon pigment is low in residual polycyclic aromatic hydrocarbons.

\* \* \* \* \*